(12) United States Patent
Petersvik

(10) Patent No.: US 6,572,541 B1
(45) Date of Patent: Jun. 3, 2003

(54) RETRACTOR SYSTEM USED IN SURGICAL OPERATIONS

(75) Inventor: Alf Petersvik, Orsta (NO)

(73) Assignee: Pular Medica AS, Bergen (NO)

( * ) Notice: Subject to any disclaimer, the term of this patent is extended or adjusted under 35 U.S.C. 154(b) by 0 days.

(21) Appl. No.: 09/462,869

(22) PCT Filed: Jul. 16, 1998

(86) PCT No.: PCT/NO98/00211

§ 371 (c)(1),
(2), (4) Date: Mar. 29, 2000

(87) PCT Pub. No.: WO99/05973

PCT Pub. Date: Feb. 11, 1999

(30) Foreign Application Priority Data

Jul. 18, 1997 (NO) .................................................. 973321

(51) Int. Cl.[7] .............................................. A61B 17/02
(52) U.S. Cl. ....................................... 600/233; 600/231
(58) Field of Search ................................ 600/201, 213, 600/215, 227, 231, 232, 233, 234

(56) References Cited

U.S. PATENT DOCUMENTS

| | | | |
|---|---|---|---|
| 2,493,598 A | | 1/1950 | Rozek |
| 3,998,217 A | | 12/1976 | Trumbull et al. |
| 4,274,398 A | | 6/1981 | Scott, Jr. |
| 4,434,791 A | * | 3/1984 | Darnell ........................ 600/233 |
| 5,052,374 A | | 10/1991 | Alvarez-Jacinto |
| 5,520,608 A | * | 5/1996 | Cabrera et al. ............. 600/201 |
| 6,042,539 A | * | 3/2000 | Harper et al. ............... 600/201 |

FOREIGN PATENT DOCUMENTS

| | | |
|---|---|---|
| DE | 1566069 | 12/1969 |
| EP | 0156218 | 10/1985 |
| WO | 9202181 | 2/1992 |

* cited by examiner

Primary Examiner—Cary E. O'Connor
(74) Attorney, Agent, or Firm—Sherman & Shalloway

(57) ABSTRACT

Retractor system to be used in surgery comprising an assistance nipple with a base plate and an adhesive patch underneath for attachment to the patient's skin or a surgical sheet, and a retractor for retracting outwardly and fastening the edges of an incision and capable of releasably fastening to the nipple, and a surgical sheet having a large opening corresponding to the surgical site with a plurality of holes surrounding the large opening through which assistance nipples may protrude. In an alternative embodiment, a ring having a plurality of nipples and adhesive to secure the ring to the patient's skin surrounding a surgical site is provided to hold a plurality of retractors.

5 Claims, 8 Drawing Sheets

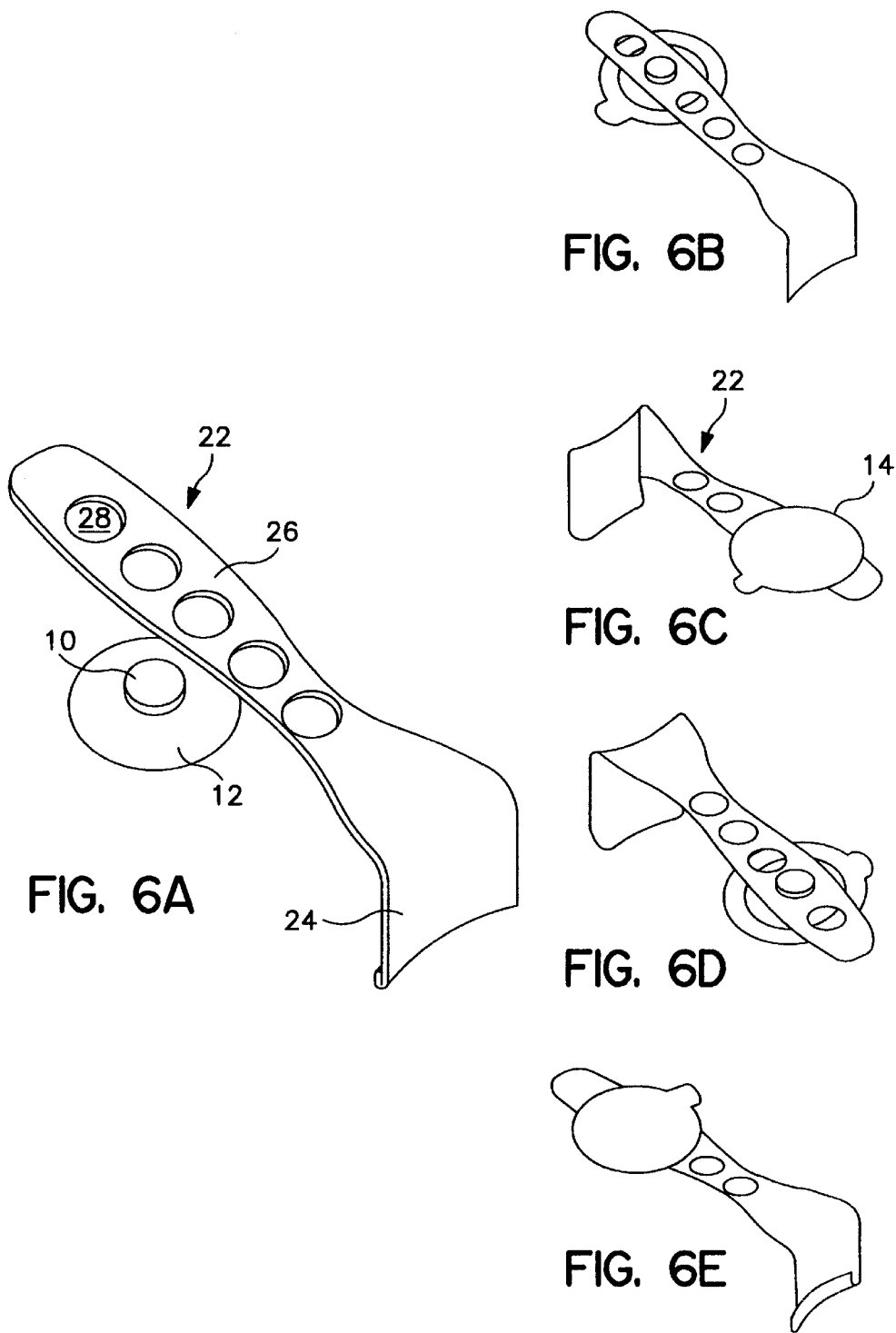

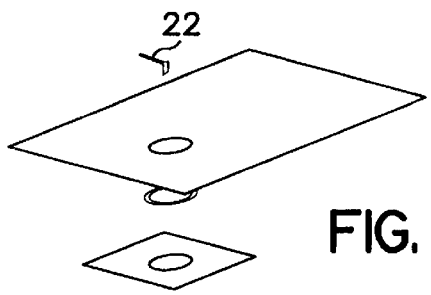
FIG. 7B
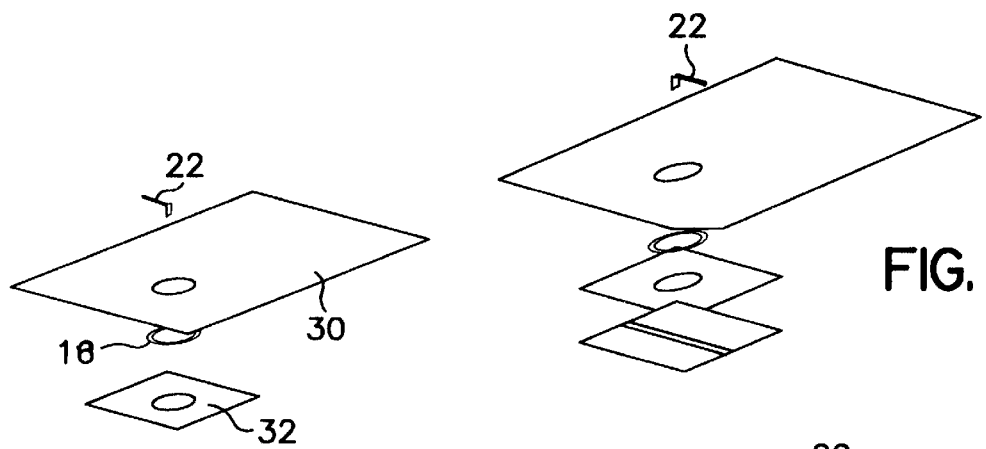
FIG. 7A
FIG. 7C
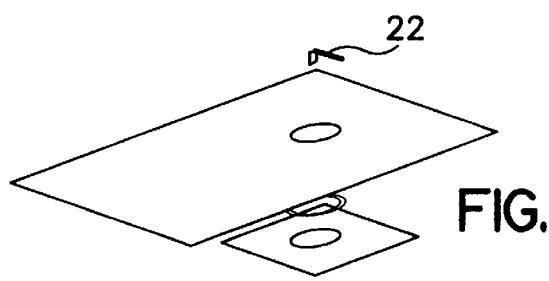
FIG. 7D
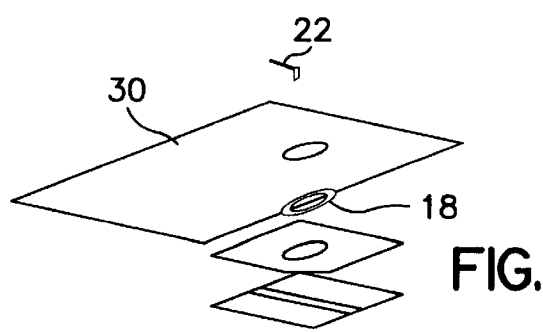
FIG. 7E

RETRACTOR SYSTEM USED IN SURGICAL OPERATIONS

The invention concerns a system for combined use of retractors and surgical sheets used for keeping a field of surgery in clear view during surgery in process. Thus, the invention concerns a system of the above-mentioned kind, comprising also an assistance nipple and an assistance ring, with a number of nipples for fastening of retractors in the decided position.

It is known, for instance during abdominal surgery, to use retractors which retract the edges of an incision apart, keeping them separated, so that the field of surgery is accessible and with unimpaired view. Previously, retractors where kept manually in desired position by surgeon assistants who also had to attend when the surgeon requested adjustment of the retractors' position. Use of retractors was therefore akward, partially strenuous and time-consuming as well as costly, due to the need for participating assistants. When used for long periods of time, it was also difficult to keep the retractors constantly in the desired position, due to variations in tension, and due to fatigue in the assistant(s).

In order to simplify the use of retractors, and decrease the need for participation from assistants, it has previously been suggested various devices for non-manual fastening of retractors and for adjustment of their position. However, it is common for all known devices that they are costly, and with complicated construction, and that they usually require two hands for positioning on a patient, and for being adjusted into position. It is also a drawback that these devices unintentionally may be brought out of position, and thus inflicting complications in ongoing surgery.

U.S. Pat. No. 2,493,598 concerns a canvas mat to be positioned over a patient's abdomen, with a relatively wide, circular opening, covering the operation area. Along the mat's longitudinal edges are straps for fastening to the lower edges of the operation table. A number of peripherally positioned retractors alongside the mat's central opening may be strapped to the opening's reinforced inner edge. The device shows none of the characteristic steps in the present invention.

U.S. Pat. No. 3,998,217 describes a flat, ring-shaped frame with four outwardly pointing peripheral support flanges, each having two fixed pegs for insertion into retractor shaft holes, through which each of four retractors may by locked in the desired position. The device is markedly different from the present invention, in which is included also retractors made from special plastic.

U.S. Pat. No. 5,052,374 describes a flat, elliptical frame to be positioned around an operation area having a number of peripheral holes. Through the holes, a number of gripping instruments and a hook instrument may be attached, for detachment with the frame. In each gripping instrument is included an upper and a lower gripping jaw, each of which are forced against one another by means of a spring, for fastening of slippery, organic tissue in the operation area. No characteristics steps present in the present invention are shown.

DE-Off.Schr. 1566069 describes a flat and slightly curved frame for positioning around an operation area, and having, on its upper side, pegs for insertion into suitable holes in retractor shafts, enabling the retractors being adjustably locked into position, in relation to the operation area. No characteristics similar to the present invention are shown.

From the summary above may be deducted that there exists a need for a retractor systems, suitable for use during surgery, and which will satisfy the requirement that need to be fulfilled by the system in question.

A suitable system of this kind must include an assistance nipple of the new type, for fastening into position on the patient's body, for fastening of a retractor, enabling retraction and fastening the edges of an incision in an operation area, where the retractor may be moved and adjusted into position using only one hand, as well as a mainly flat assistance ring, for positioning around an operation area, having mounted assistance nipples of the above-mentioned type for insertion into holes in the retractor shafts, so that the retractors may be replaced into different positions, allowing the incision edges to be retracted and fastened into different positions in relation to the operation area. These positions must be adjustable, through repositioning of the retractors by use of one hand only, so that the assistance nipples on the assistance frame may be inserted into other shaft holes. The assistance frame is used in combination with a surgical sheet, having an opening for the operation field. Both the assistance nipples, as well as the assistance ring and the retractors having shafts with holes are made from non conductive, acid and impact resistant plastic material. Retractors, assistance nipples and assistance rings made form said material are not known beforehand, and are therefore novel, separate elements in combination according to the invention's system.

A requirement for use is also that the system's single parts easily may be cleaned and sterilized for use.

According to the invention, a retractor system has been presented, and it is characterized in the claims below.

Reference is made to the drawings, where

Figure 4:
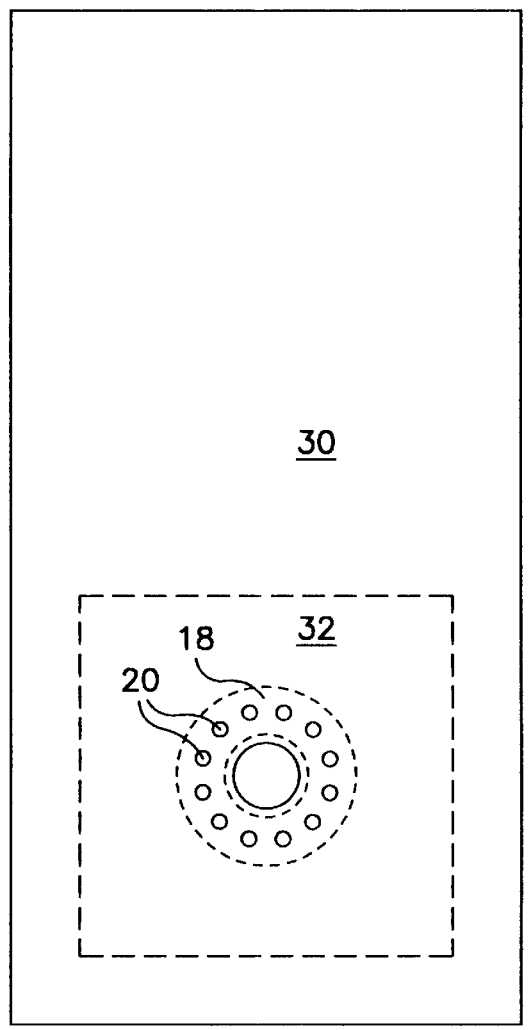
Figure 5:
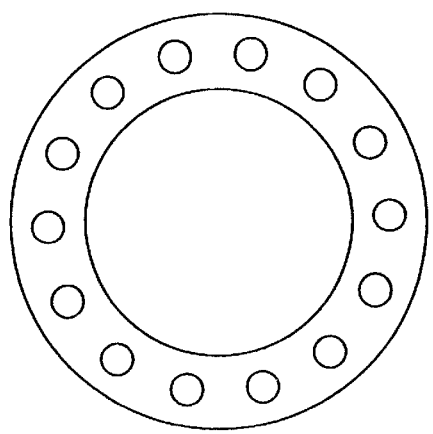

FIG. 4 a plan view from above, showing a surgical sheet in combination with a plastic assistance ring according to the invention FIG. 5 an enlarged plan view of the assistance ring with attached nipples according to the invention FIG. 6*a* shows, in perspective, a plastic retractor and a plastic assistance nipple in perspective with the adhesive patch according to the invention.

FIGS. 6*b* and 6*d* shows the retractor and assistance nipple in perspective and seen from above.

FIGS. 6*c* and 6*e* shows the same parts in perspective and seen from below.

FIG. 7*a* shows in perspective a plastic retractor with plastic assistance ring and surgical sheet with adhesive patch according to the invention.

FIGS. 7*b* and 7*d* shows the parts according to FIG. 7*a* in perspective and seen from above.

FIGS. 7*c* and 7*e* shows the parts according to FIG. 7*a* in perspective and seen from below.

Figure 8B:
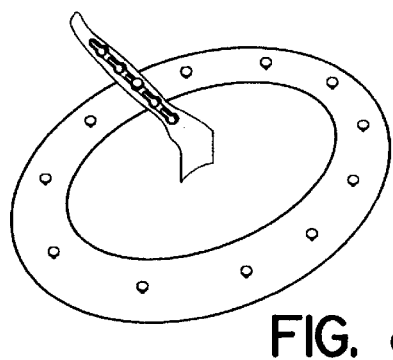
Figure 8A:
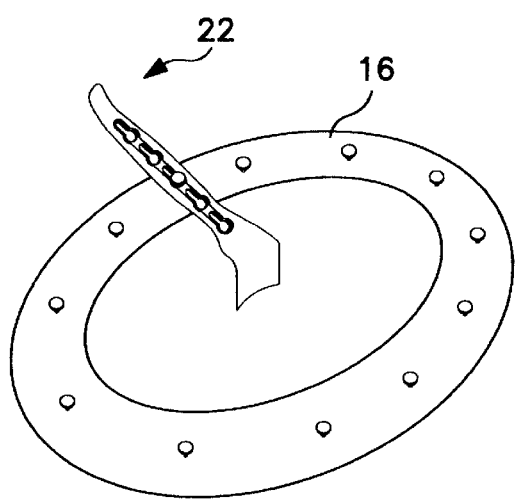

FIG. 8*a* shows in perspective an assistance ring with a retractor according to the invention.

Figure 8C:
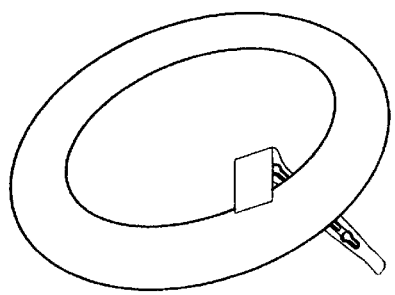
Figure 8D:
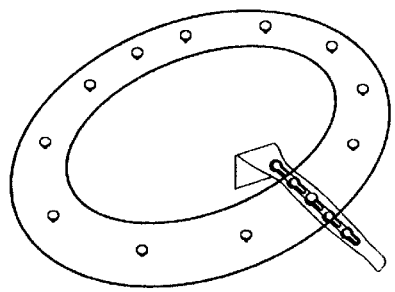

FIGS. 8*b* and 8*d* shows the same parts in perspective and seen from above.

Figure 8E:
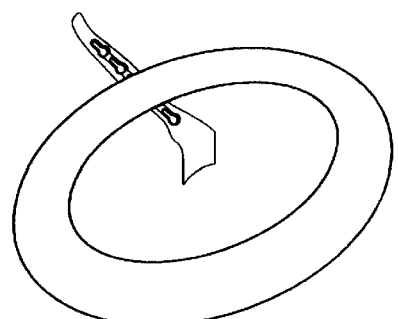

FIGS. 8*c* and 8*e* shows the same parts in perspective and seen from below.

Figure 9:
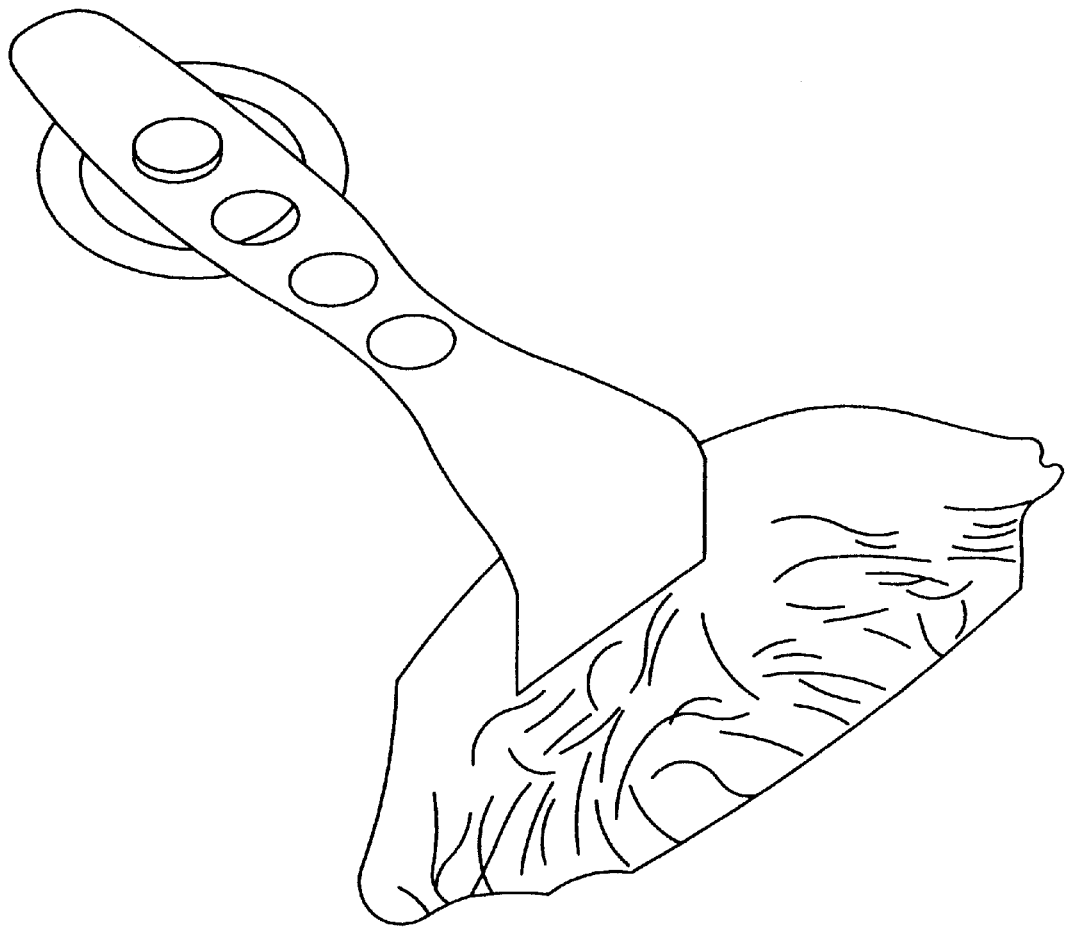

FIG. 9 shows a single assistance nipple in use.

Figure 10:
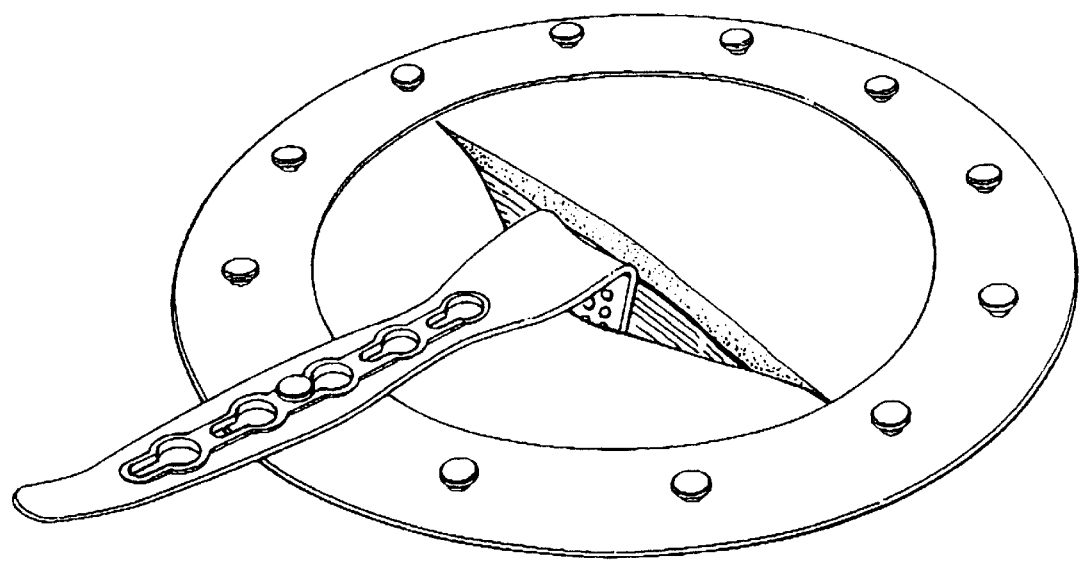

FIG. 10 shows an assistance nipple in use.

The depicted retractor system "Easyhold" according to the invention comprises, in a preferred embodiment of the invention, an assistance nipple 10 made from non conductive, acid, heat and impact resistant plastic material, made in one piece, with a base 12, attached underneath with an adhesive patch 14 for fastening to the skin of a patient, for instance in preparation to abdominal surgery. By means of a plastic retractor 22 according to the invention, the edge of an incision may be retracted outwardly to the extent desired, so that the operation area is accessible and in clear view. The retractor is kept in position by one of several holes 28 in the retractor shaft 26 being pulled over the outwardly protruding assistance nipple 10. The retractor 22 may, if necessary, be repositioned, by detaching the shaft 26 from the assistance nipple 10 and selecting and pulling a different shaft hole 28 over the nipple 10, all by using only one hand.

Figure 1:
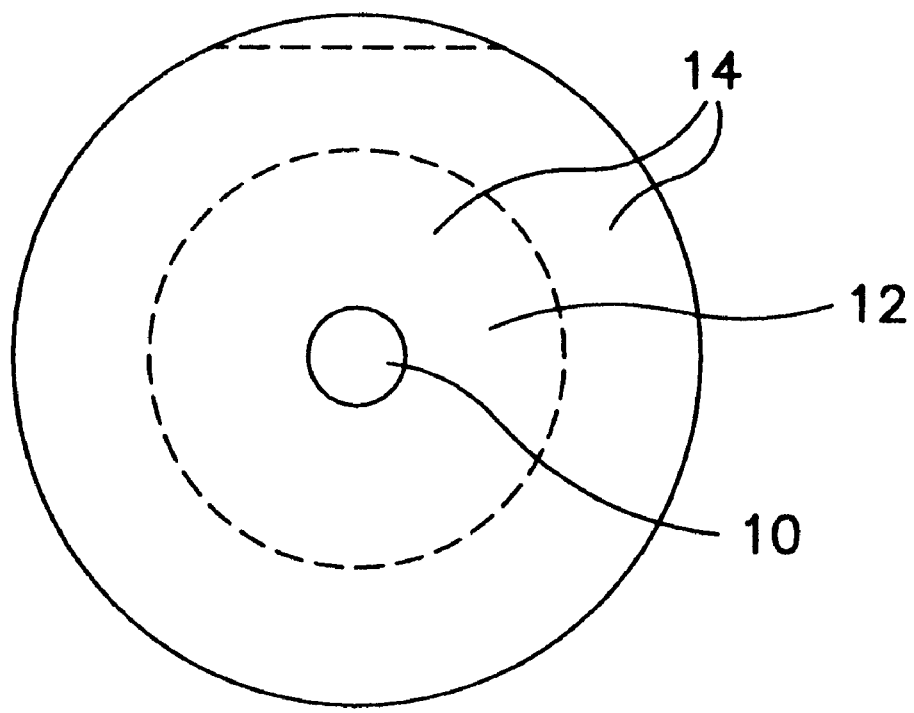
FIG. 1 shows a plan drawing of an assistance nipple according to the invention
Figure 2:
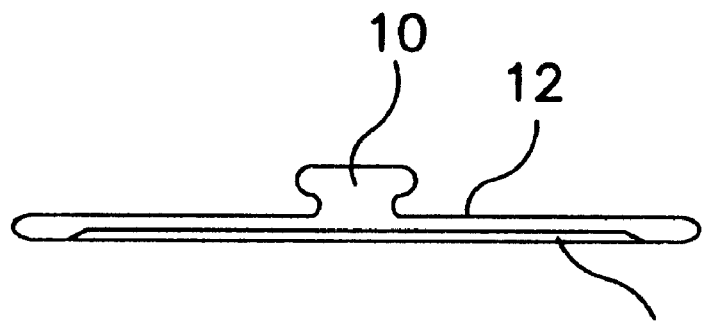
FIG. 2 shows a plan view of the nipple according to FIG. 1
Figure 3:
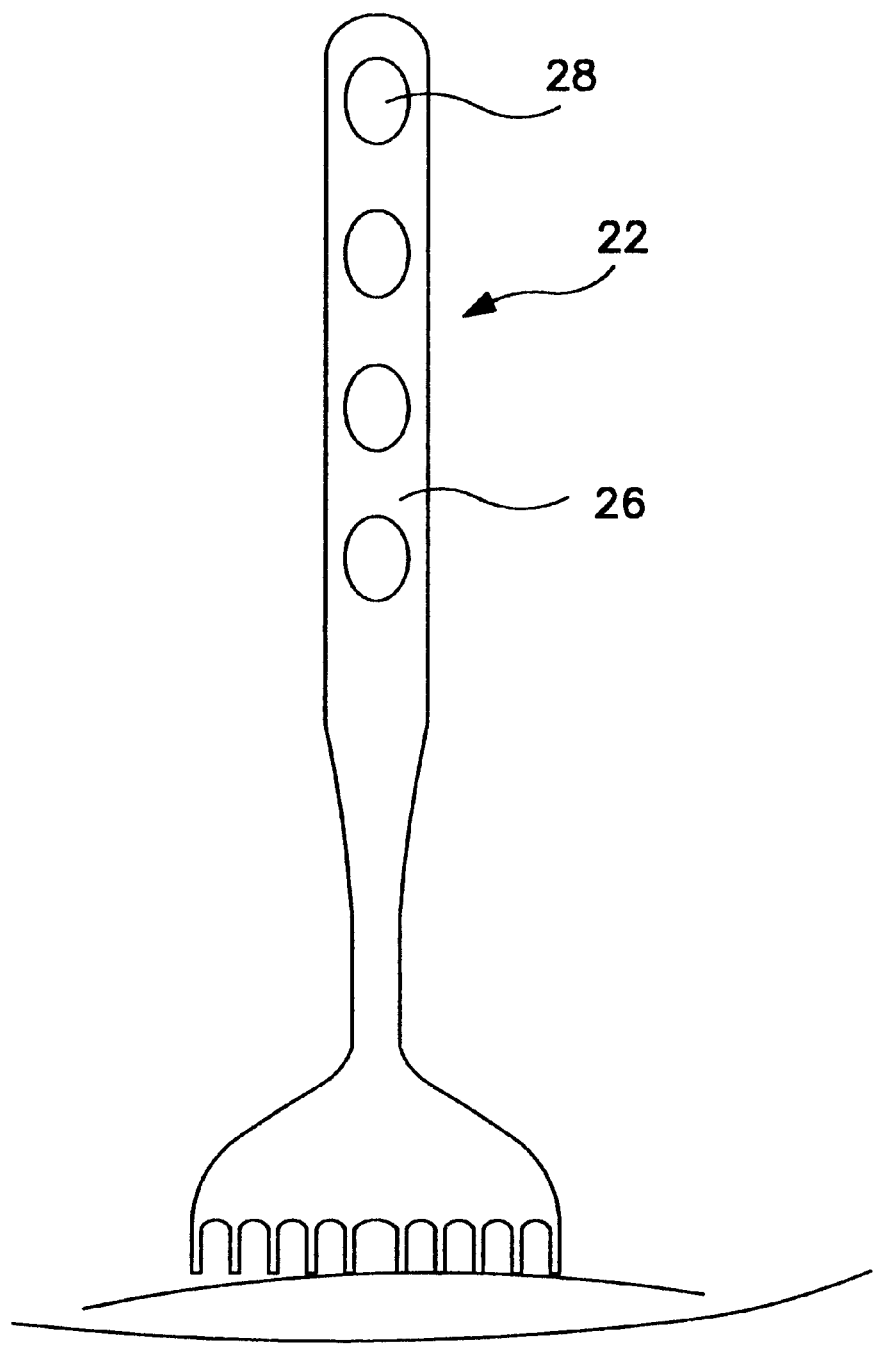
FIG. 3 shows a plan view of a plastic retractor according to the invention

In the system according to the invention is also included an assistance ring 18 of the above-mentioned special plastic material, having a number of mounted assistance nipples 20, as well a one or several retractors 22, also being made from special plastic material, another kind shown in FIG. 3. The retractor 22 comprises a gripping part 14, and a shaft 26 with several holes 28 for attaching assistance nipples 10 and 20 respectively, for fastening of the retractor.

By means of the plastic retractor(s) 10 (22) according to the invention, the edges of an incision may be pulled outwardly to a desired extent so that the operation area is assessable and in clear view. The retractor is kept in position by one of several holes 28 in the retractor shaft 26 being pulled over the outwardly protruding assistance nipple 10 or 20. The retractor 22 may, if necessary, be repositioned, by detaching the shaft 26 from the assistance nipple 10 and selecting and pulling a different shaft hole 28 over the nipple 10 (20), all by using only one hand.

Further, the system includes a plastic surgical sheet 30 with a middle opening surrounded by a number of peripheral holes arranged to have the same distance from one another as the nipples 20 on the assistance ring 18 and with an adhesive patch 32 beneath, having a middle opening, corresponding to the opening of the surgical sheet 30 and of the assistance ring 18 for use and preparation to an operation the assistance ring 18 is placed underneath the opening of the surgical sheet, and on top of the opening of the adhesive patch, where by the adhesive patch is fasten to the patient's skin with the opening placed around the operation field and with the nipples 20 on the assistance ring 18 protruding upwards through the holes of the surgical sheet 30. The retractor 22 may thereafter be attach to the assistance ring nipples, in the decide position according to the operational field. The retractors positioning my also be adjusted through use of one hand only.

Advantages to be mentioned in the invention are that the single parts of the system are made preferably from non conductive, impact, acid and heat resistant plastic material which easily may by cleaned and sterilized for reuse, and which will decrease the risk of the patient suffering wounds by use of diathermia and a possible subsequent infection. The need for personal use for keeping retractors in the desired position during surgery in progress is no longer required.

Assisting surgery personnel may instead perform other operations at the same time, which are not static, and do not cause occupationally related injuries. The total time required for different types of surgery may therefor be reduced. All of the above may result in sick leaves caused by injuries in surgery personnel, reduced health insurance costs, and not least, in decreased waiting time for patients in need of surgery, thereby improving the overall economy in society.

What is claimed is:

1. A retractor system for use in surgery comprising:

an assistance member having an upper surface and a lower surface, the upper surface having at least one nipple protruding upward therefrom, at least one retractor comprising a shaft having a tissue engagement means at one end, the shaft having a plurality of nipple mating holes disposed longitudinally therealong capable of releasably receiving and mating with the at least one nipple on the assistance member whereby the retractor is removably attachable to the assistance member, at least one fastening means applied to the lower surface of the assistance member engaging a patient's skin surface whereby the assistance member and retractors attached thereto are securely fastened to the skin of the patient thereby avoiding detrimental movement during surgery, wherein the fastening means comprises a double sided adhesive patch of a size at least sufficient to cover the lower surface of the assistance member, and a surgical sheet having a large opening therein corresponding to a surgical site, and a plurality of holes disposed about the periphery of the large opening and of a size to permit passage of the nipples therethrough wherein the assistance member is positioned on the patient beneath the sheet such that the nipples protrude through the holes and the fastening means is of a size greater than the lower surface of the assistance member to engage and secure the surgical sheet relative to the assistance member.

2. The retractor system of claim 1 wherein the assistance member comprises a frame adapted to surround the surgical site and having a plurality of nipples substantially equidistantly spaced thereon, the fastening means comprising a double sided adhesive patch substantially matching the lower surface of the assistance member in size and shape and bonded thereto.

3. The retractor system of claim 2 further comprising a surgical sheet having a large opening therein corresponding to a surgical site and the area bounded by the frame, and a plurality of holes spaced from the periphery of the large opening and matching the location of the plurality of nipples on the frame whereby the nipples extend through the holes when the frame is placed on the patient and the sheet is placed over the frame.

4. The retractor system of claim 3 wherein the fastening means has an area extending beyond at least the outer periphery of the frame between the sheet and the patient whereby the sheet is adhered to the patient with the frame.

5. The retractor system of claim further comprising a surgical sheet having a large opening therein corresponding to a surgical site and a plurality of holes disposed about the periphery of the large opening and of a size to permit passage of the nipples therethrough.

* * * * *

UNITED STATES PATENT AND TRADEMARK OFFICE
CERTIFICATE OF CORRECTION

PATENT NO.     : 6,572,541 B1
DATED          : June 3, 2003
INVENTOR(S)    : Alf Petersvik It is certified that error appears in the above-identified patent and that said Letters Patent is hereby corrected as shown below:

<u>Title page,</u>
Item [73], Assignee, change "Pular Medica AS" to -- Polar Medica AS --

Signed and Sealed this

Twenty-third Day of September, 2003

JAMES E. ROGAN
*Director of the United States Patent and Trademark Office*